(12) United States Patent
Stauffer

(10) Patent No.: US 8,507,735 B2
(45) Date of Patent: Aug. 13, 2013

(54) ALCOHOL SYNTHESIS

(76) Inventor: John E Stauffer, Greenwich, CT (US)

(*) Notice: Subject to any disclaimer, the term of this patent is extended or adjusted under 35 U.S.C. 154(b) by 182 days.

(21) Appl. No.: 13/166,050

(22) Filed: Jun. 22, 2011

(65) Prior Publication Data

US 2012/0330071 A1    Dec. 27, 2012

(51) Int. Cl.
*C07C 29/149* (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS 4,122,110 A * 10/1978 Sugier et al. .................. 518/713
7,947,746 B2 * 5/2011 Daniel et al. .................. 518/700

* cited by examiner

*Primary Examiner* — Elvis O Price
(74) *Attorney, Agent, or Firm* — Young Basile Hanlon & MacFarlane PC

(57) ABSTRACT

A process is disclosed for the production of alcohols including ethanol, propanol and butanol starting with lower molecular weight alcohol, which is reacted with carbon monoxide to give an organic acid that in turn is reduced with hydrogen to form the product.

4 Claims, 2 Drawing Sheets

ALCOHOL SYNTHESIS

FIELD OF THE INVENTION

The present invention relates to a process for the manufacture of an alcohol including ethanol, propanol and butanol from an alcohol with one less carbon atom. In the process, an alcohol and carbon monoxide are reacted together in the gas phase over a heterogeneous catalyst to produce the alcohol product. By repeating this process, any alcohol in the homologous series can be made starting with methanol.

BACKGROUND OF THE INVENTION

There are two principal routes for the commercial production of ethanol. One procedure is based on petrochemical technology. Starting with ethylene, ethanol is produced by means of the catalytic hydration of this olefin.

The second method for ethanol synthesis relies on the fermentation of sugar, derived either from corn or sugar cane. A major drawback to fermentation processes is the fluctuation in the cost of commodities used as raw materials.

Propanol, or more specifically n-propyl alcohol, is manufactured by the oxo process. In this operation, ethylene is reacted with carbon monoxide and hydrogen to give propanal. This aldehyde is then reduced with hydrogen, resulting in the product, propanol.

The oxo process is also used to produce butanol. In this case, propylene is treated with carbon monoxide and hydrogen in the presence of a catalyst to give butyraldehyde. This intermediate is then reduced to produce isobutyl alcohol as well as some n-butyl alcohol.

Alternatively, butanol can be produced by fermentation. Increased attention is being paid to this technology because of the interest in renewable materials.

SUMMARY OF THE INVENTION

A process is provided for the production of an alcohol including ethanol, propanol and butanol from an alcohol with one less carbon atom. The process is conducted in two steps.

First, an alcohol feed is vaporized and passed together with carbon monoxide over a heterogeneous catalyst to produce an organic acid. The catalyst comprises rhodium promoted with either iodide or triphenylphosphine. The reaction is carried out at a temperature in the range of 250° C. to 350° C. and a pressure from 1 to 65 atmospheres.

Second, the organic acid produced in the first step is produced in the first step is reduced with hydrogen over a catalyst of copper chromite to give the alcohol product plus water. The reaction temperature is in the range of 200° C. to 300° C. and the pressure is between 1 and 100 atmospheres.

The alcohol product from the second step is separated from the water and purified to meet specifications. By recycling this alcohol, the process can be repeated to make a higher molecular weight alcohol.

Other advantages, features and characteristics of the present invention, as well as methods of operation and functions of the related elements of the structure, and the combination of pails and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawings wherein like reference numerals refer to like parts throughout the several views and wherein.

DETAILED DESCRIPTION OF THE PROCESS

The process of the present invention comprises two distinct chemical reactions carried out sequentially. These reactions can be expressed by the following equations.

$$ROH + CO \rightarrow RCOOH \quad (1)$$

$$RCOOH + 2H_2 \rightarrow RCH_2OH + H_2O \quad (2)$$

When the above equations are added together, the following expression is obtained.

$$ROH + CO + 2H_2 \rightarrow RCH_2OH + H_2O \quad (3)$$

In the above equations, R stands for a radical including $CH_3$, $C_2H_5$, and $C_3H_7$.

Equation 3 represents the overall reaction of the process. It shows that an alcohol combines with carbon monoxide and hydrogen to give a new alcohol with one more carbon atom plus water.

The standard preparation of organic acids of carbonylation is shown by equation 1. Also known as the oxo process, alcohol reacts with carbon monoxide to produce an acid. Over the years many catalysts have been reported for this reaction, all of which required relatively high temperatures and pressures.

A breakthrough occurred in carbonylation when a low pressure process was developed for acetic acid. This process is based on a rhodium catalyst promoted with iodide. With this improvement, reaction temperatures as low as 150° C. to 200° C. and pressure in the range of 33 to 65 atmospheres are possible. In other reports, a rhodium catalyst promoted with triphenylphosphine was disclosed for preparing propanal in an oxo process.

The reduction of an organic acid to an alcohol is shown in equation 2. Although this reaction is disclosed in the literature, it is not considered to be practical. Instead, the acid should first be converted to an ester by reacting it with an alcohol. This ester readily reacts with hydrogen to form two alcohols, one of which corresponds to the acid from which the ester is made.

The preferred catalyst for the reduction is copper chromite although various nickel-based catalysts have been reported. The reaction temperature is in the neighborhood of 250° C. Because the hydrogenation of esters is often performed in the liquid phase, high pressures of hydrogen are used. In the present invention, however, this reaction is carried out in the gas phase so that a more modest pressure is available.

Since carbon monoxide can poison the hydrogenation catalyst, all traces of this reactant should be removed prior to the reduction step.

Figure 1:
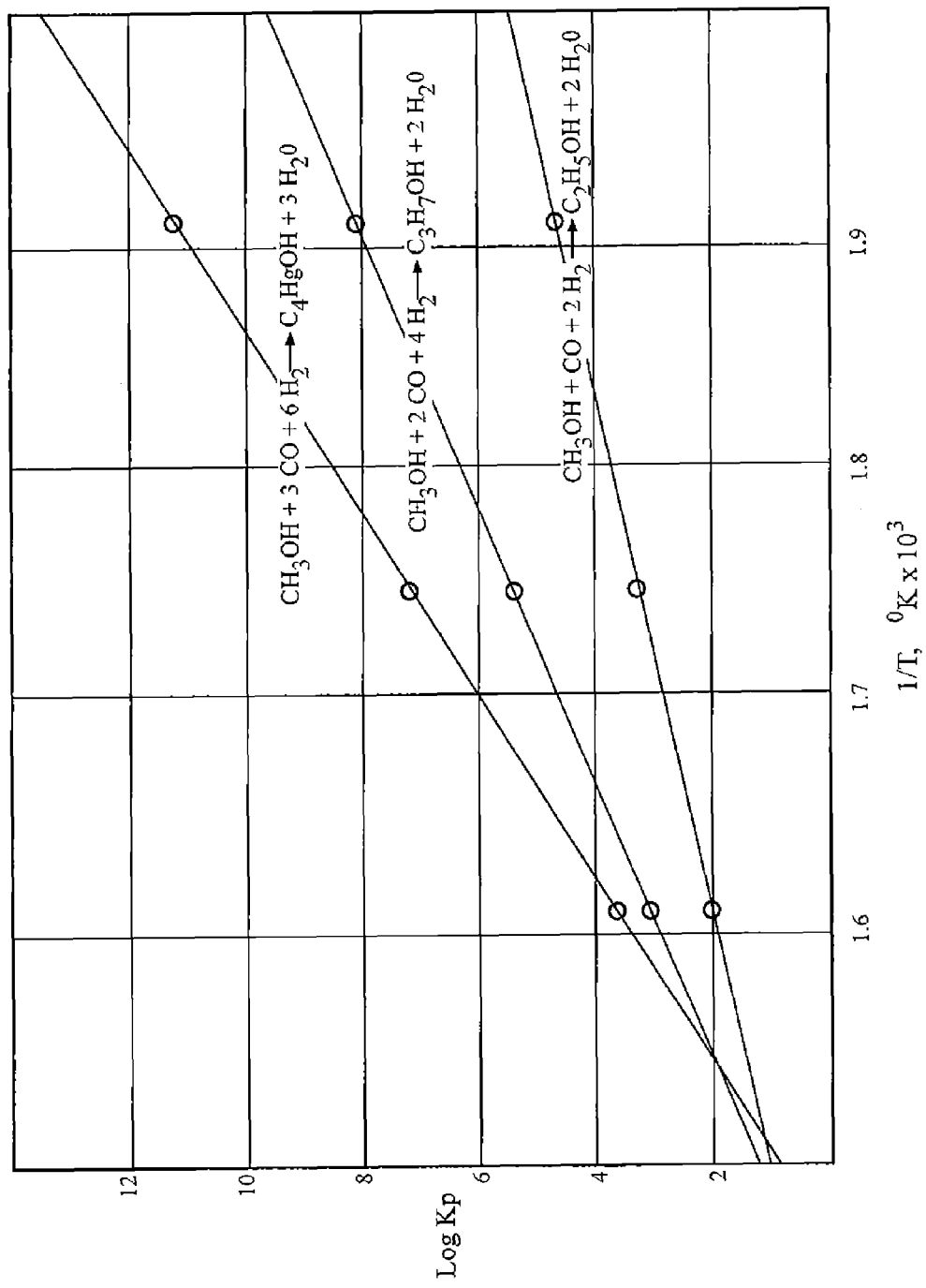
FIG. 1 is a graph showing the thermodynamic results for combined processes beginning with methanol as the feedstock.

The present invention can be configured so as to produce any one of the alcohol products starting with methanol. In order to achieve this objective, the intermediate alcohols are recycled until the final alcohol is obtained. When this arrangement is used, the net reaction consists of the reaction of methanol with carbon monoxide and hydrogen to produce the desired alcohol. The equilibrium conditions for producing ethyl alcohol, n-propyl alcohol and isobutyl alcohol by this process are shown in FIG. 1. It should be noted that the conversions are more favorable for the higher alcohols.

Figure 2:
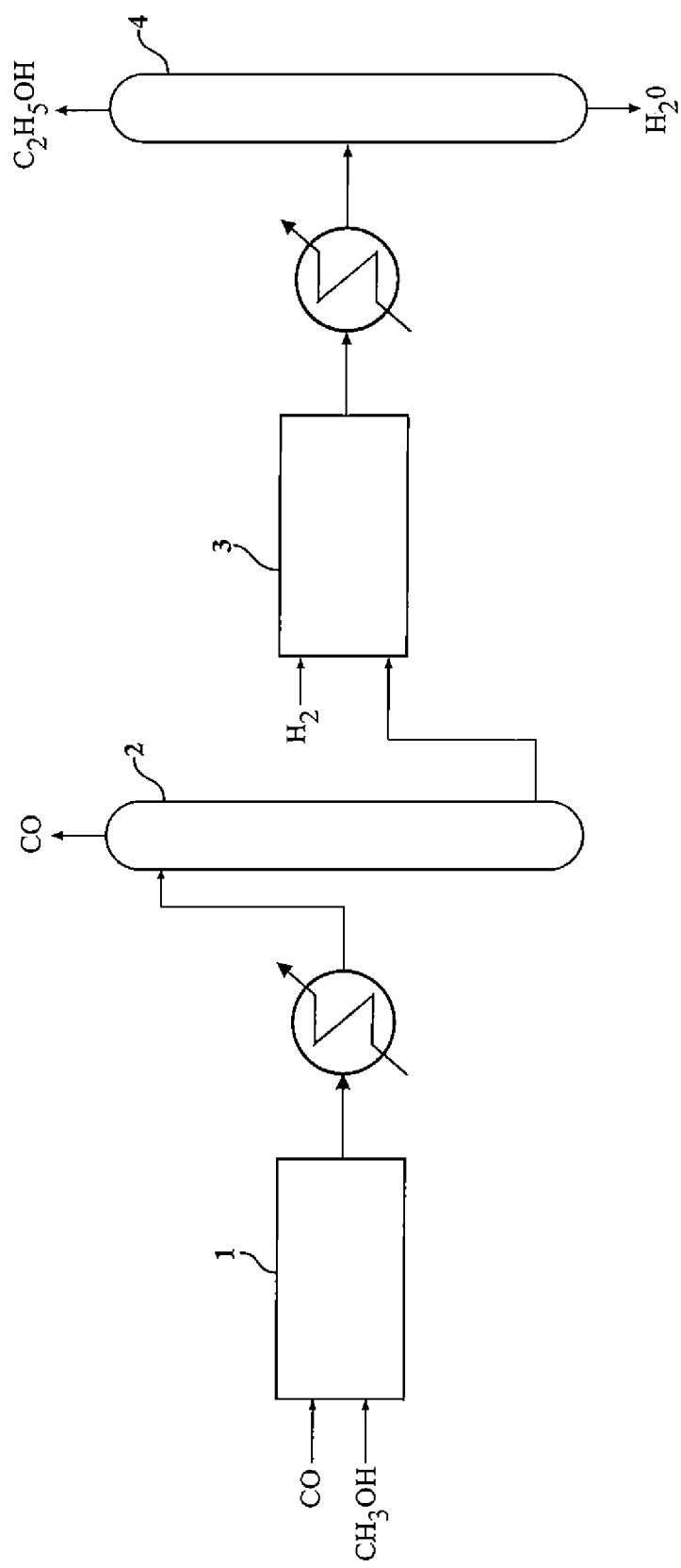
FIG. 2 is a flow sheet is one embodiment of the process.

A better appreciation of the present invention can be gained by referring to FIG. 2. This block diagram shows one application of the process, namely, the synthesis of ethanol. At the front end, methanol vapor and carbon monoxide are fed to oxo reactor 1. The effluent from this reactor is cooled and sent to stripper 2 where traces of carbon monoxide are removed from the acetic acid. This intermediate plus hydrogen are introduced to hydrogenation reactor 3, in which case the acetic acid is reduced to ethanol. The product gases are cooled and passed to distillation column 4 to separate the alcohol from water.

The flow sheet for producing higher alcohols is much the same as for ethanol except that the fractionation of the alcohol is different. Because of the closeness in boiling points and possible azeotropes, an extraction step may be used. In addition, provision must be made to form the ester of the organic acid produced in the oxo reactor. The methyl ester can be formed by introducing methanol ahead of the hydrogenation reactor.

One of the main attractions of the present invention is from freedom from any reliance on the use of olefins as reactants. This advantage will become increasingly important as the costs of petrochemicals continue to rise. Neither does the present invention depend on fermentation which competes with the food supply for raw materials.

What is claimed is:

1. A process for the manufacture of an alcohol product comprising the steps of:
   the reaction of alcohol, containing one less carbon atom than the product, with carbon monoxide over a promoted rhodium catalyst at a temperature in the range of 250° C. to 350° C. and pressure from 1 to 65 atmospheres to produce an organic acid; and
   the reaction of the organic acid from the first step with hydrogen over a copper chromite catalyst at a temperature in the range of 200° C. to 300° C. and a pressure between 1 and 100 atmospheres, to give the alcohol product and water, which are separated by fractionation.

2. A process according to claim 1 wherein the alcohol product is ethanol.

3. A process according to claim 1 wherein the alcohol product is propanol.

4. A process according to claim 1 wherein the alcohol product is butanol.

\* \* \* \* \*